(12) United States Patent
Hammer et al.

(10) Patent No.: US 6,753,297 B2
(45) Date of Patent: Jun. 22, 2004

(54) USE OF INDOLE-3-SUCCINIC ACID AS AUXIN

(76) Inventors: Charloc Hammer, 2017 Calle Lejano, Santa Fe, NM (US) 27501; Daniel Armstrong, 3124 Almond Rd., Ames, IA (US) 50014

(*) Notice: Subject to any disclaimer, the term of this patent is extended or adjusted under 35 U.S.C. 154(b) by 0 days.

(21) Appl. No.: 10/326,752

(22) Filed: Dec. 20, 2002

(65) Prior Publication Data

US 2003/0158043 A1 Aug. 21, 2003

Related U.S. Application Data

(60) Provisional application No. 60/343,107, filed on Dec. 21, 2001.

(51) Int. Cl.$^7$ ................... A01N 43/38; C07D 209/18
(52) U.S. Cl. ................................ 504/284; 548/494
(58) Field of Search ..................... 504/284; 548/494

(56) References Cited

U.S. PATENT DOCUMENTS 6,361,999 B1 * 3/2002 Lin et al. ................ 435/410

OTHER PUBLICATIONS

Hui et al. "High–performance liquid chromatographic and capillary electrophoretic enantioseparation of plant growth regulators and related indole compounds using macrocyclic antibiotics as chiral selectors" Journal of Chromatography A. 906:91–103. 12 J.*

Matsuda et al. "Control of Bacterial Wilt of Tomato Plants by a Derivative of 3–Indolepropionic Acid Based on Selective Actions on Ralstonia solanacearum". Journal of Agricultural and Food Chemistry. 46:4416–4419. 1998.*

* cited by examiner

*Primary Examiner*—S. Mark Clardy
(74) *Attorney, Agent, or Firm*—Muserlian, Lucas and Mercanti

(57) ABSTRACT

Indole-3-succinic acid and its derivatives are used as auxins. They are administered to plants to promote root growth.

9 Claims, 6 Drawing Sheets

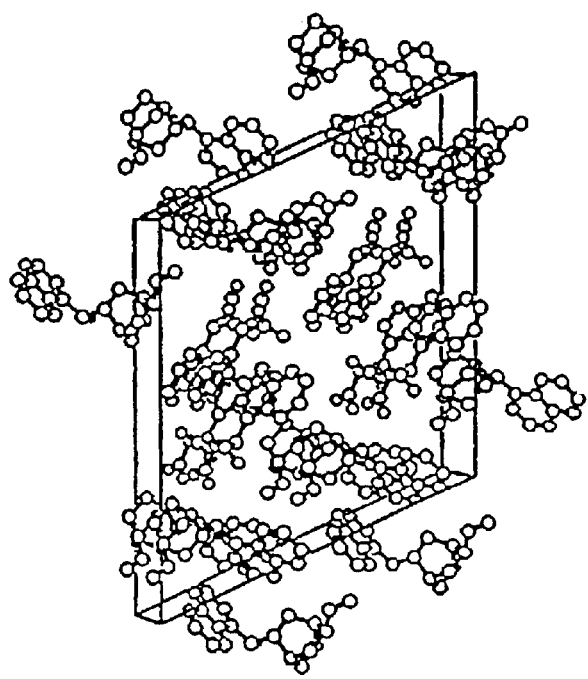
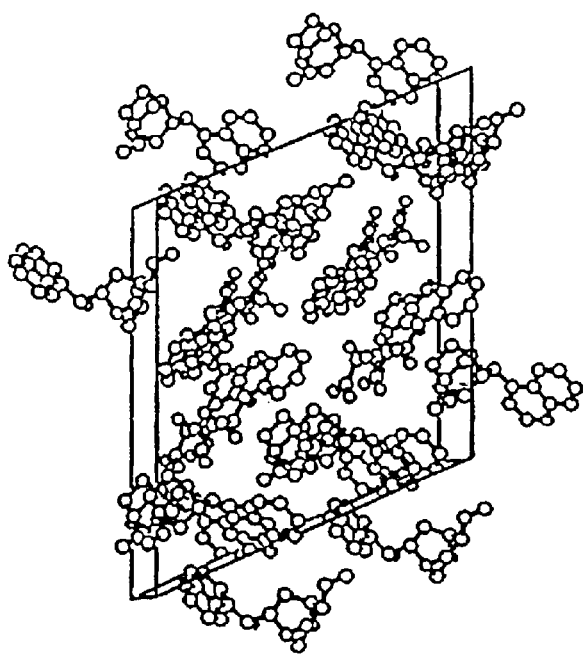
Fig. 3

USE OF INDOLE-3-SUCCINIC ACID AS AUXIN

The present application claims the priority of US provisional patent application No. 60/343,107 filed Dec. 21, 2001.

BACKGROUND OF THE INVENTION

1. Field of the Invention

This invention relates to auxins, growth hormones for plants and, more particularly, to the new use of indole-3-succinic acid and its derivatives as an auxin.

2. Art Relating to the Invention

Auxins are well-known plant growth or development hormones, that were first extensively studied in the mid 1930's. Auxins are involved in a variety of plant activities although their ability to promote cell elongation is perhaps best known. The most widely occurring, natural auxin in indole-3-acetic acid (IAA). It occurs in both free and conjugated states in plants and seeds. Early on, the use of IAA was shown to be advantageous in stimulating root formation in plant cuttings. Subsequently, synthetic materials such as indole-3-butyric acid (IBA) and naphthleneacetic acid (NAA) were found to be even more useful at least in part, due to their greater stability. Most recently it has been found that IBA also occurs naturally in some plants albeit at very low levels. Today IBA and NAA are widely used as synthetic rooting hormones. They are most often applied to the base of plant (stem and leaf) cuttings, and to transplantings since it is known that auxins are required for initiation of adventitious roots on stems, and to stimulate root growth in general. Rooting hormones are widely used for plant propagation because they hasten root initiation, improve rooting percentages, produce more uniform rooting, and increase the number and quality of roots.

SUMMARY OF THE INVENTION

It has now been discovered that indole succinic acid (indole-3-succinic acid) and its derivatives can be used as an auxin.

Hereinafter, the term ISA will be used to refer to indole-3-succinic acid and it derivatives while the individual names as recited herein will be used when referring to an individual compound, such as indole-3-succinic acid.

It has also been discovered that ISA is more effective in promoting growth of some seedlings than either the natural auxin IAA or the synthetic auxins IBA and NAA.

It has furthermore been discovered that both enantiomers alone of ISA and the racemate (racemic mixture) of ISA act as auxins and that either enantiomer alone of ISA and/or the racemate of ISA have a greater effect on root growth than either IAA or IBA. It has also been discovered that enantiomers ISA have different effects on the root growth of different plants.

Furthermore, it is surprising and unexpected that the enantiomers and the racemate have different effects on plant growth than each other.

Broadly, the present invention is directed to the new use of ISA as an auxin. The present invention is a method for promoting growth in plants comprising treating a plant with an effective amount of ISA to promote growth in the plant.

ISA which are capable of this new use, can be represented as follows:

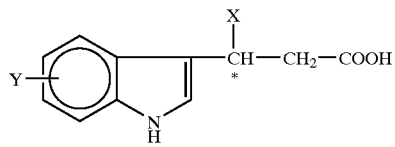

wherein:

Y is a hydrogen (H), a hydroxyl group (OH), a halogen, a nitro group ($NO_2$), a sulfinate group ($SO_3$), an alkyl group or an aryl group, and X is a carboxylic acid group (COOH), a carboxylic acid ester group ($COOR_1$), an acetyl group ($CH_2COOH$) or an aryl group.

*The asterisk denotes a stereogenic center which means the compound can exist in two different enantiomeric forms.

Suitable halogens include fluorine (F), chlorine (Cl) and bromine (Br).

Suitable ester groups ($R_1$) include alkyl groups.

Suitable alkyl groups for both Y and $R_1$ include $C_1$ to $C_6$ alkyl groups, straight chained or branched, i.e. methyl, ethyl, propyl, butyl, pentyl and hexyl.

Suitable aryl groups include both one and two aromatic rings, e.g. phenyl and naphthyl.

Specific ISA's that can be employed in the present invention include:

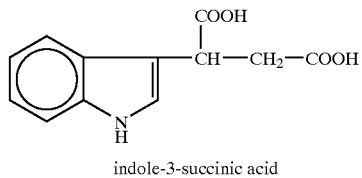

indole-3-succinic acid

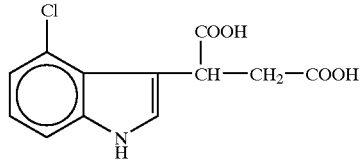

4-chloroindole succinic acid

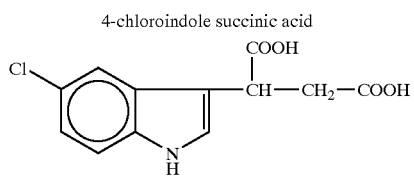

5-chloroindole succinic acid

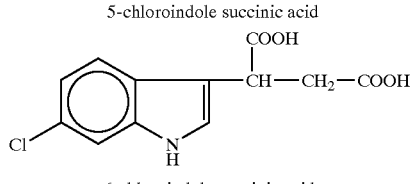

6-chloroindole succinic acid

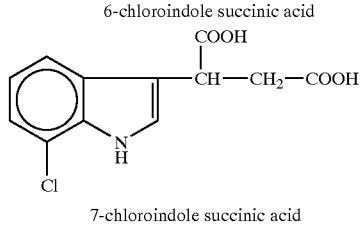

7-chloroindole succinic acid

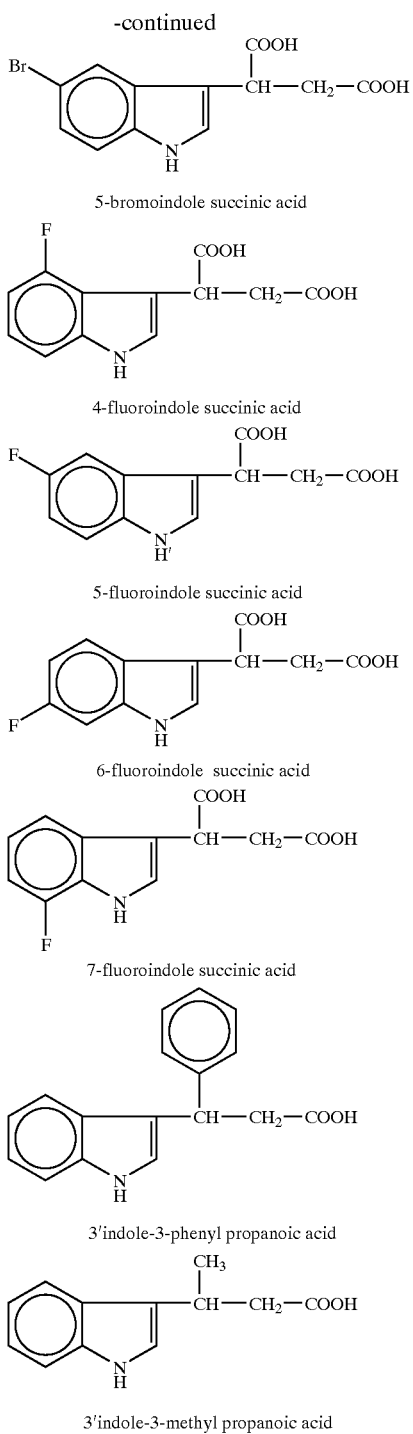

-continued 5-bromoindole succinic acid 4-fluoroindole succinic acid 5-fluoroindole succinic acid 6-fluoroindole succinic acid 7-fluoroindole succinic acid 3'indole-3-phenyl propanoic acid 3'indole-3-methyl propanoic acid As noted above, ISA is much more effective in promoting growth of some seedlings than either the natural auxin, IAA, or the widely used synthetic hormones IBA and NAA. However, unlike the other rooting hormones, ISA contains one stereogenic center, and can exist in two enantiomeric forms. Most chiral biologically active compounds are known to be stereoselective and it is known that enantiomers can have different biological actions and potencies. However, there have been few reports on enantioselective growth-promoting auxins. Indole-3-succinic acid has been synthesized only as the racemate, it has never been resolved into individual enantiomers, until now.

It has been discovered that the auxin activity of ISA is stereoselective, and both ISA enantiomers individually and the racemate act as auxins and can have the same or greater effect on root growth than either the natural auxin, IAA, or the most widely used synthetic analogue, IBA.

Treating the plant with ISA to promote growth in the plant is accomplished in a conventional manner using conventional equipment. Suitably, the plants can be grown hydrophonically, or the plant can be dipped into a solution of the auxin or still further the soil in which the plant grows can be treated with the auxin. The seed can also be coated with the auxin in a conventional manner with the auxin, however, this does not appear to work as well as the other three methods.

Treating the soil-is accomplished in a conventional manner using conventional equipment. It can be plowed into the ground, potting soil can be used which contain ISA or the hole into which the plant is placed can be sprayed with ISA.

The amount of ISA administered to the plant is an effective amount to promote growth in the plant. Suitably, the amount administered to the plant is a conventional amount, conventional in the sense of comparable to the amount of known auxins that are administered to plants to promote growth, however, lesser amounts can be used of ISA than conventional auxins to obtain comparable results in certain instances.

Suitably, ISA is administered as an aqueous solution either alone or with other additives. The optimum concentration range for ISA in solution is about $10^{-5}$ to about $10^{-9}$ M when the plant is grown hydroponically.

When the plant is dipped into an aqueous solution, the concentration of ISA in the solution is suitably about 0.001 to about 0.1% (weight percent). When the soil is treated, either by plowing it into the ground, adding it to the potting soil, or just spraying it into the ground into which the plant will be grown, the concentration of the ISA in the aqueous solution is suitably about one part per thousand to about one part per trillion (about $10^3$ ppm to about $10^{-6}$ ppm).

Other additives which can be included in the aqueous solution include nutrients such as nitrogen or phosphors, fungicides, herbicides and insecticides.

As noted, ISA can be administered as either enantiomer alone or as a racemate. ISA is suitably administered as a salt or any conventional form. ISA can be administered with acceptable carriers as is conventional with auxins.

ISA as well as the salts are made in a conventional manner using conventional equipment. The separation of the individual enantiomers from the racemate is likewise accomplished in a conventional manner using conventional equipment.

The term racemate or racemic mixture is an equal mix of both enantiomers. However, a mix in any amount or proportion of the two enantiomers can be used as well. Likewise, the ISA need not be pure enantiomers or pure racemate.

It has been found that racemic ISA is easily synthesized and can be resolved both chromatographically and by crystallization as the diastereomeric cinchonidine salt. The absolute configuration of its enantiomers can be determined by x-ray diffraction. Both enantiomers of ISA and its racemate have significantly greater "root growth promoting activity" than the popular IBA and the naturally occurring auxin IAA on the plants-tested. It has also been found that the (R) and (S)-enantiomers of ISA can have different activities with respect to plant growth.

Since different plants do not respond in the same way to all auxins, in some plants it will be beneficial to use racemic ISA. This is because a mixture of these two stereoselective growth promoters can elicit a broader range of responses than other conventional synthetic auxins that currently are-in use.

BRIEF DESCRIPTION OF THE DRAWINGS

These and other aspects of the present invention may-be more fully understood by reference to one or more of the following drawings wherein:

FIG. 3 illustrates the crystal packing for the unit cell of the (S)-indole-3-succinic acid cinchonidine salt;

DETAILED DESCRIPTION OF THE INVENTION

The synthesis of ISA produces a racemic mixture. This compound can be photodeactivated (this causes plants to grow toward light-one form of phototropism). Also, ISA can undergo racemization and decomposition at extremes of pH, and at higher temperatures. A simple, highly efficient analytical resolution of indole-3-succinic acid can be achieved by HPLC using an appropriate chiral stationary phase (see FIG. 1). With this method, enantiomeric purities can be determined to >99.9% for both enantiomers.

Figure 1:
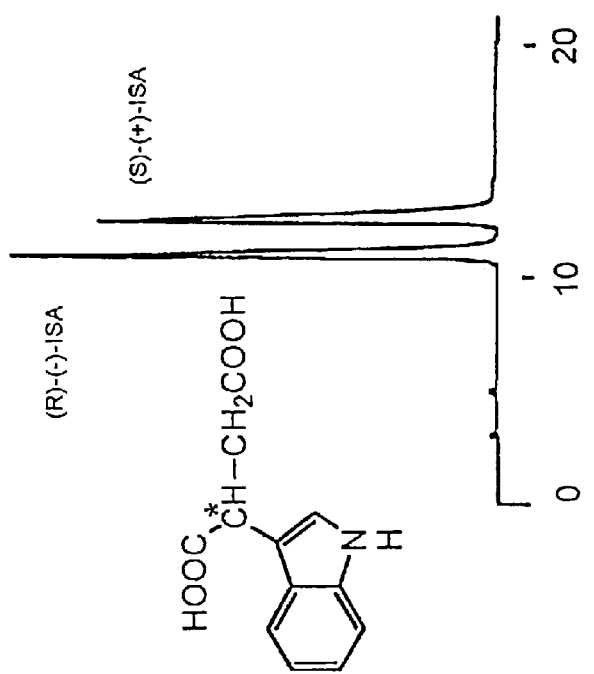
FIG. 1 illustrates a LC chromatogram showing the separation of indole-3-succinic acid enantiomers.
Figure 2:
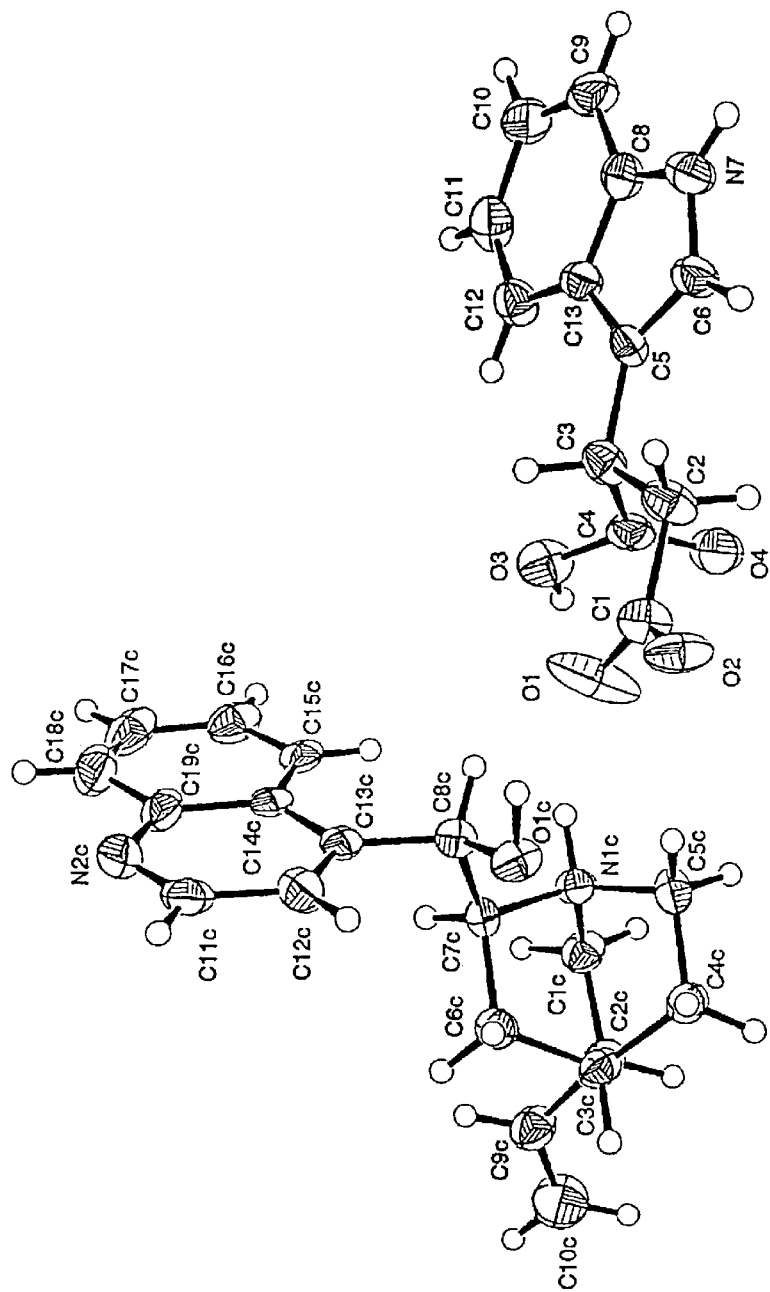
FIG. 2 illustrates the x-ray crystal structure of the (S)-indole-3-succinic acid cinchonidine salt.

In FIG. 1, a LC chromatogram of indole-3-succinic acid is shown. The separation of the enantiomers was on a Cyclobond I-RSP column (25 cm×0.46 cm (i.d.) Using a mobile phase of 40:60:02 (v:v:v) methanol:water:glacial acetic acid (flow rate=1.0 ml/min). The optical rotation of the compound represented by each peak was determined with an on-line laser polarimeter. The absolute configuration was determined as indicated in FIGS. 2 and 3. FIG. 2 illustrates the x-ray crystal structure of the (S)-indole-3-succinic acid cinchonidine salt, while FIG. 3 illustrates the crystal packing for the unit cell of the (S)-indole-3-succinic acid cinchonidine salt.

Although the chromatographic separation is simple, effective, and can be used to determine enantiomeric purities, it does not allow for determination of the absolute configuration of the enantiomers of ISA. ISA can be resolved in large quantities by recrystallization as the (−) cinchonidine salt. The enantiomeric purity of the crystallized product can be determined by chromatographic method. FIG. 2 shows the structure (and absolute configuration) of one enantiomer of indole-3-succinic acid (as the cinchonidine salt). This enantiomer has the S-configuration, and corresponds to the second peak in FIG. 1. FIG. 3 shows the packing of the unit cell for the diastereomeric salt. Since the stereochemistry of the cinchonidine alkaloid is known, the determination of the absolute configuration of indole-3-succinic acid was greatly simplified (FIGS. 2 and 3).

Figure 4A:
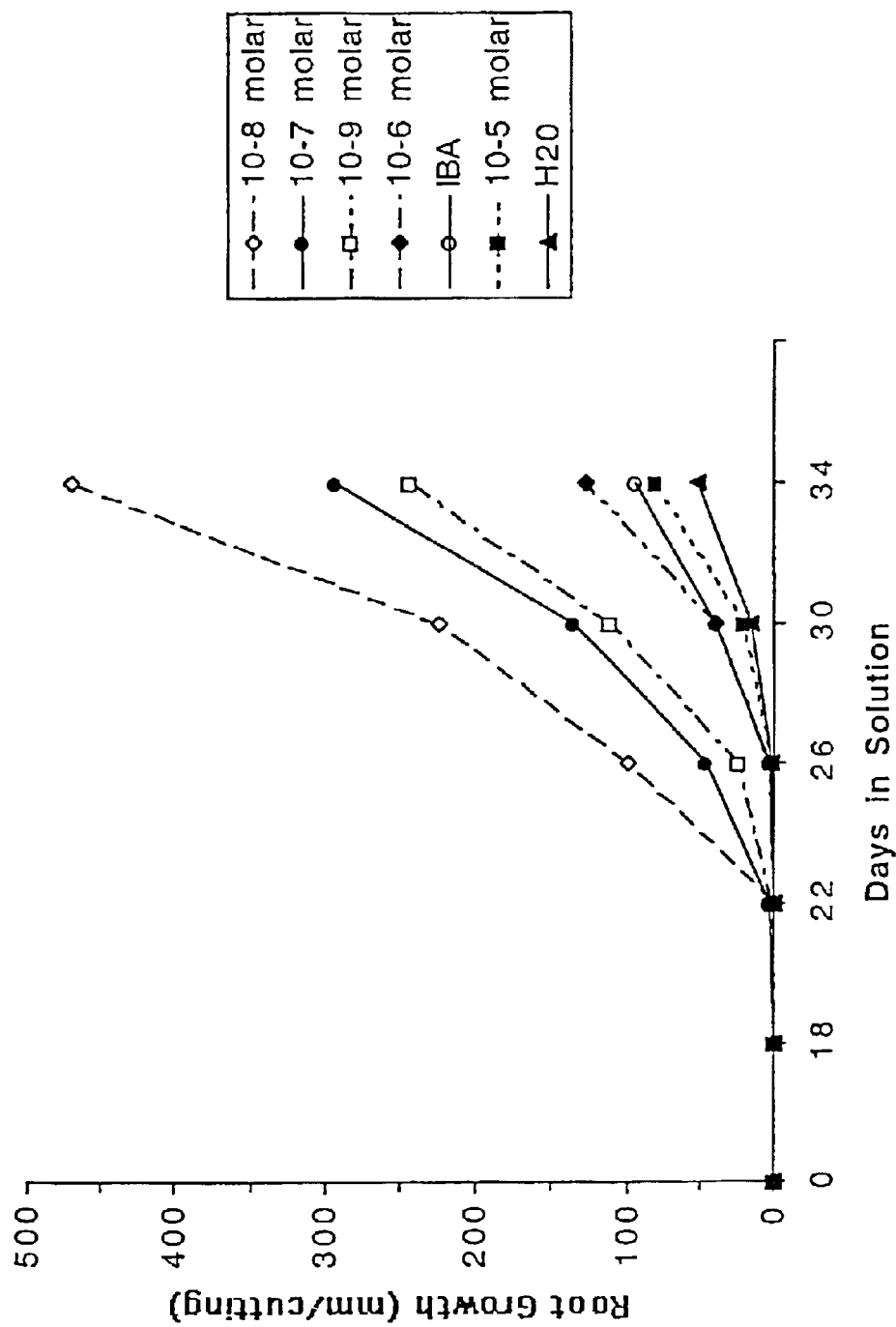
FIG. 4a illustrates the effect of different concentrations of (R)-indole-3-succinic acid, IBA and water on the root growth of Swingtime Fuchsia.
Figure 4B:
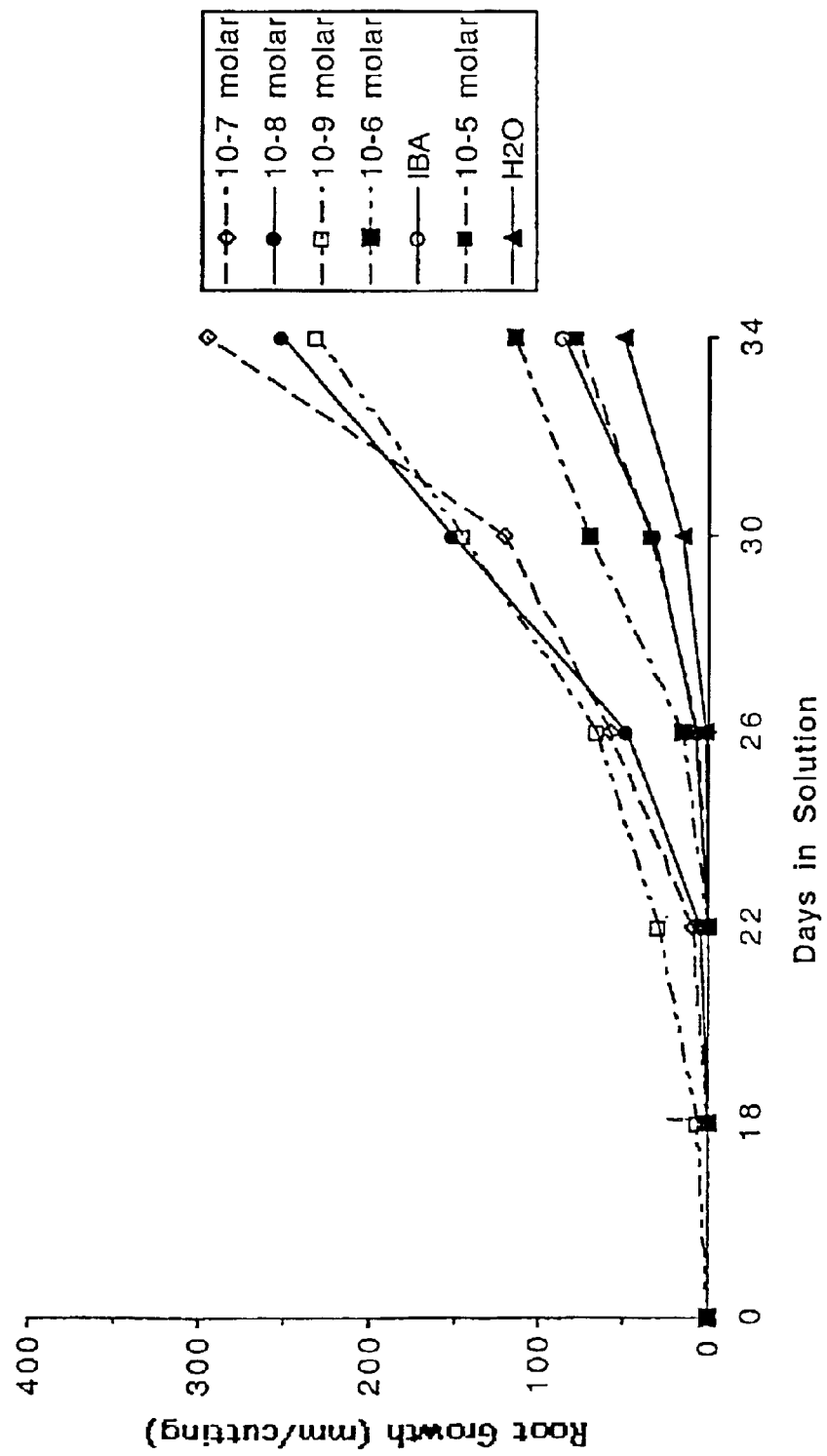
FIG. 4b illustrates the effect of different concentrations of (S)-indole-3-succinic acid, IBA and water on the root growth of Swingtime Fuchsia.

FIG. 4a shows the effect of different concentrations of (R)-indole-3-succinic acid, labelled ISA, as well as IBA, on the root growth of Swingtime Fuchsia. FIG. 4b shows the effect of different concentrations of (S)-indole-3-succinic acid, labelled ISA, as well as IBA, on the root growth of Swingtime Fuchsia. There is an optimum concentration range that produces the greatest effect for each synthetic auxin. The growth curve for deionized water ($H_2O$) is also shown.

FIGS. 4a and 4b show typical results for the total root growth of Swingtime Fuchsia. This data illustrates several trends. First, the ISA activity is very concentration dependent, as are all natural and synthetic auxins. The maximum effect for both a solution of ISA enantiomers is in the range of $10^{-5}$ to $10^{-9}$ M. Concentrations of ISA either above or below this range have much less effect. Indeed, it is well-known that higher concentrations (above optimal levels) of both natural and synthetic auxins can have an inhibiting effect on root growth. The (R) and (S)-enantiomers of ISA can have different effects, as shown in FIGS. 4a and 4b.

Finally, root growth tends to occur earlier and proceeds more prolifically for plants exposed to the optimal amounts of ISA than either untreated plants or plants treated with the recommended concentration of the synthetic auxin IBA. As is known, the effects of any single plant growth hormone can vary between plant species, and even strains. It has been found that $10^{-8}$ M of the R-enantiomer of ISA is more potent for Swingtime Fuchsia while the opposite enantiomer is observed to be more potent for Varigated Fuchsia at all concentrations of ISA (see FIG. 5). Determination of the optimal amount for any plant is done in a conventional manner.

Figure 5:
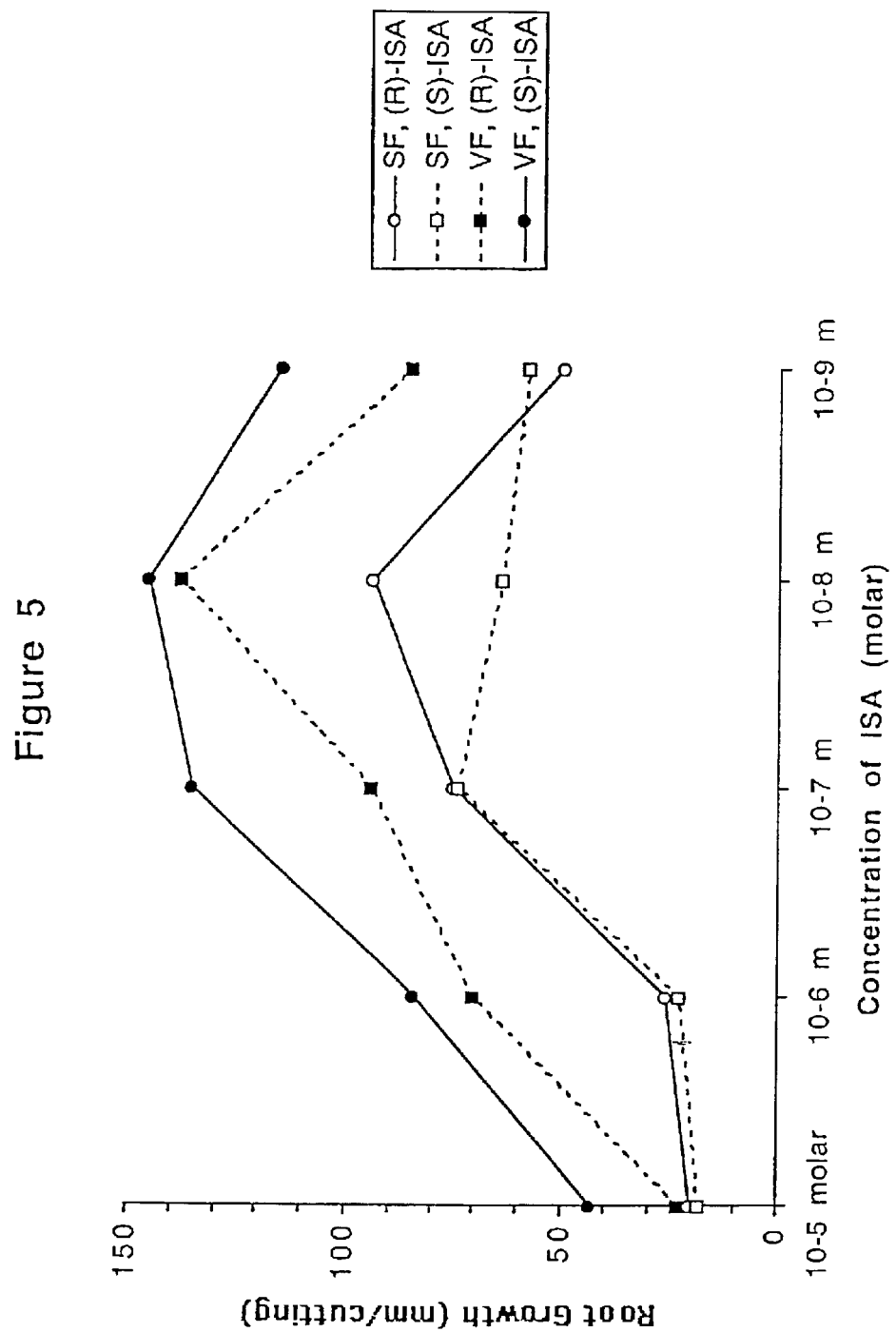
FIG. 5 illustrates the effect of different concentrations of (S)-indole-3-succinic acid and (R)-indole-3-succinic acid on root growth of Swingtime Fuchsia (SF) and Varigated Fuchsia (VF).

FIG. 5 shows the effect of different concentrations of (S)-indole-3-succinic acid, labelled (S)-ISA and (R)-indole-3-succinic acid, labelled R-ISA on root growth of Swingtime Fuchsia (SF) (bottom two curves with the open symbols) and Varigated Fuchsia (VF) (top two curves with the solid symbols). The optimum concentration for these synthetic auxins is in the $10^{-7}$ to $10^{-8}$ molar range. Also, these two varieties of Fuchsia appear to have the opposite ISA enantioselectivity.

EXAMPLE 1

This example illustrates making indole-3-succinic acid, the separation of enantiomers by chromatography, the optical resolution of the racemate and the crystalline data as illustrated in FIGS. 1–3.

Preparation of Indole-3-Succinic Acid 14.57 g (0.1486 mole) of Maleic anhydride was dissolved in 11.0 mL of ethyl acetate, and then 34.81 g (0.297 mole) of indole was added with magnetic stirring. The deep orange-red solution was stirred until all the indole went into the solution. Yellow-orange crystals formed after standing at 4° C. for 2 days. Filtration and washing with ethanol (10 mL) gave 28.48 g (yield 58%) of yellow-orange crystals of maleyl diindole. The 28.48 g (0.0857 mole) of maleyl diindole was refluxed for 3 hours with 30% aqueous potassium hydroxide solution (150 mL). The reaction mixture was cooled and extracted with ether, and the ether was evaporated, yielding crude indole (10.050 g, 0.08858 mole). The alkaline solution was acidified to pH 4.4 with conc. sulfuric acid. After removal of water under reduced pressure, the residue was subject to soxlet extraction with 250 mL of methyl-tert-butyl ether for 36 hours, which gave racemic indole-3-succinic acid, 11.96 g (yield 60%). Recrystallization from ethanol-water yielded pale pinkish white platelets, m.p.: 196–198° C. (with gas evolution). (lit., m.p.: 197–198° C.).

All reagents were commercially available and obtained from conventional sources. The synthesis of ISA was conventional.

Chromatography An assembled HPLC system was used to separate racemic indole-3-succinic acid. It consisted of a LC-6A pump, a SPD-2AM UV detector, and a CR 601 Chromatopac recorded from Shimadzu (Kyoto, Japan). The analytical column used in this study was a Cyclobond I 2000 RSP column, 250×4.6 mm (i.d.) Obtained from Advanced Separation Technologies, Inc. (Whippany, N.J.) as was the analogous semi-preparative Cyclobond I 2000 RSP 500×10 mm (i.d.). The mobile phase was methanol/water/acetic acid (30:70:0.1, volume ratio) and the flow rate was 1 ml/min. The detection wavelength was 254 nm. Chiral LC was used to confirm the enantiomeric purity of the products. The optical rotation (at 675 nm) of the eluted enantiomers was determined with an in-line chiroptical LC detector (i.e, the PDR Chiral Advanced Laser Polarimeter, Palm Beach Gardens, Fla.). The results are illustrated in FIG. 2. In most cases, this rotation correlates with that found for the sodium D-line. Elemental analysis was performed by Galbraith Laboratories, Inc. (Knoxville, Tenn.). Melting points were determined on a Thomas-Hoover capillary melting point apparatus, and were uncorrected. The absolute configuration was confirmed by x-ray crystallography as outlined below.

Optical Resolution of Racemic Indole-3-Succinic Acid by Preferential Crystallization as Cinchonidine Salts A mixture of 1.26 g (4.29 mmole) of cinchonidine and 1.00 g (4.29 mmole) of racemic indole-3-succinic acid in 10 mL of 96% ethanol was heated on a steam bath with magnetic stirring until all of the solid dissolved. The solution was cooled slowly to room temperature, and the white precipitate formed was collected and washed with ether. After 11 recrystallizations from 96% ethanol and one solution of 96% ethanol:methanol, 80:20 by volume, and drying, colorless fine needles of (S)-indole-3-succinic acid-cinchonidine salt was obtained. 0.296 g, yield: 13.1%, ee: 99.3%. Mp: 196–198° C. (with gas evolution). Elemental analysis: Calculated for $C_{31}H_{33}N_3O_{55}$: C=70.57%, H=6.30%, N=7.96% Found: C=70.00%; H=6.42%; N=7.84%. IR: 3500–2900, 1592, 1460 cm-1. By fractional removal of (S)-indole-3-succinic acid salt, followed by rotary evaporation of the solvent and recrystallization (supra vide), the (R)-indole-3-succinic acid-cinchonidine salt was obtained.

The ammonium salts of both indole-3-succinic acid enantiomers were obtained by suspending the respective indole-3-succinic-cinchonidine salts in concentrated aqueous $NH_4OH$. As the suspension was heated, the solid dissolved. When the solution was cooled to room temperature, cinchonidine precipitated from the solution. After removal of the precipitate, the volume of the supernatent liquid was reduced by rotary evaporation. Additional cinchonidine precipitated when this solution was cooled to room temperature. This process was repeated if any cinchonidine was left in solution (as determined by reversed phase-LC using a 250X 46 mm, id, ASTEC $C_{18}$ column). The ees of (S)-indole-3-succinic acid and (R)-indole-3-succinic acid were found to be 98% and 94% respectively, as determined by enantioselective HPLC (FIG. 1). The enantiomeric excess (ee) is calculated as follows: ee=(A−B)/(A+B)×100 where 'A' is the predominant enantiomer, and 'B' is its antipode.

Crystallographic Data for Cinchonidine Indole Succinate Salt

X-ray diffraction analysis was carried out on a Siemens SMART CCD system at 173 K. The structure of the salt $(C_{19}H_{23}N_2O^+C_{12}H_{10}NO_4$, MW 527.60 amu) was determined from an orthorhombic crystal of dimensions 0.355× 0.1×0.1 mm$^3$ (space group $C_2$), with unit cell a=20.0944(2) Å, b=6.6716 Å, c=22.294(2) Å, β=113.646(2)°, V=2737.8 (4) Å, Z=4, $D_x$=1.28 g cm$^{-3}$, m=0.087 mm$^{-1}$. The absolute configuration was determined by the known stereochemistry of the cinchonidine. Mo Kα (λ−0.71070 Å). 3696 reflections, 2253 with I>3σ(I), R=0.058.

EXAMPLE 2

This example illustrates the auxin effect of each indole-3-succinic acid enantiomer and indole-3-succinic acid racemate, and compares them to IBA and water. The results are shown in FIGS. 4a, 4b and 5. A detailed description of this root growth study follows.

Fresh solutions were used in each experiment. Weights of hormone salts were measured to ±0.01 mg on a Mettler H-16 single-pan mechanical balance (reproducibility=±0.03 mg). Using indole-3-succinic acid R and S enantiomers as the 2×$NH_4^+$ salt, 1.40 mg, was dissolved in 95% ethanol (20 mL) and slowly diluted to 500 mL with deionized water to make a stock solution of 1.047×10$^{-5}$ molar concentration. Dilutions were then made in the following manner.

10$^{-5}$ molar 50 mL stock solution used directly

10$^{-6}$ molar 5.0 mL stock solution+45.0 mL R.O. water

10$^{-7}$ molar 0.50 mL stock solution+49.5 mL R.O. water

10$^{-8}$ molar 0.50 mL of 10$^{-6}$ molar solution+49.5 mL R.O. water

10$^{-9}$ molar 0.50 mL of 10$^{-7}$ molar solution+49.5 mL R.O. water

For the concentration study (S)-indole-3-succinic acid; 2NH$^{4+}$ (98% e/e, 1.41 mg), and IBA Na(1.13 mg) were used to make stock solution of 1.055×10$^{-5}$ and 1.005×10$^{-5}$ molar, respectively. Deionized water was also used as a control.

Five new-growth cuttings of two different varieties of *Fuchsia hybrida* (i.e., Varigated Fuchsia and Swingtime Fuchsia) were placed into the 50 mL solutions contained in orange plastic pill containers that were blackened with black electrician's tape. The solutions were placed in a fiberglass solar prism greenhouse (90% of UV light is filtered out of sunlight) in which the temperatures varied from 55° F. (night) to 100° F. (day). The solutions were topped with deionized water daily to the 50 mL mark to compensate for water expiration and evaporation. Readings of the root growth were measured in total mm for the cuttings in a particular solution on days 7, 10, 14, 18, 22, 26, 30, and 34. These were recorded as the number of rootlets/total length (mm). Occasionally one cutting from the groups of five did not survive. Therefore, all data reflect the average mm root growth per survived cutting.

EXAMPLE 3

This example compares indole-3-succinic acid enantiomers and ISA racemate to IBA and IAA. Table 1 below illustrates the results. More specifically, Table 1 illustrates the relative effectiveness (in promoting root growth) of different indole-3-succinic acid solutions compared to 10$^{-7}$ M indole-3-butyric acid (IBA) and a 10$^{-7}$ M IBA solution.

TABLE 1

| Compound[a] | Concentration (M) | Plant Tested[b] | Enhancement Ratio[c] |
|---|---|---|---|
| (S)-ISA | $10^{-7}$ | VF | 3.8 |
| (S)-ISA | $10^{-7}$ | SF | 5.7 |
| (S)-ISA | $10^{-8}$ | VF | 4.6 |
| (S)-ISA | $10^{-8}$ | SF | 4.8 |
| (R)-ISA | $10^{-7}$ | VF | 0.7 |
| (R)-ISA | $10^{-7}$ | SF | 5.6 |
| (R)-ISA | $10^{-8}$ | VF | 4.4 |
| (R)-ISA | $10^{-8}$ | SF | 7.1 |
| Racemic ISA | $10^{-7}$ | SF | 7.0 |
| IAA | $10^{-7}$ | VF | 0 |
| IAA | $10^{-7}$ | SF | 0 |

[a]The abbreviations for three compounds are: (S)-ISA = (S)-indole-3-succinic acid, (R)-ISA = (R)-indole-3-succinic acid, IBA = indole-3-butyric acid, and IAA = indole-3-acetic acid.
[b]The abbreviations for the plant types are: VF = Varigated Fuchsia and SF = Swingtime Fuchsia.
[c]The relative effectiveness or enhancement ratio (R) was calculated using the following formula: $R = (ISA_x - H_2O)/(IBA - H_2O)$ where $ISA_x$ is the average root growth obtained per cutting with $ISA_x$ solution. IBA is the average root growth per cutting with IBA and $H_2O$ is the average root growth per cutting with only deionized water.

Table 1 is a comparison of the relative potencies of various forms of indole-3-succinic acid (i.e, the (R)-enantiomer, (S)-enantiomer and racemate), and the commercial synthetic auxin indole-3-butyric acid (IBA). In every case but one, both enantiomers and racemate had significantly higher activity than the IBA. In one case, a higher than optimum level of $10^{-7}$ M (R)-indole-3-succinic acid had nearly the same activity as the optimum level of IBA. Also included in Table 1 is the relative potency of racemic IAA (a $10^{-7}$ M solution). Its potency is significantly higher than that of IBA as well. It should be noted that the level of each enantiomer in the racemate is about half that of the corresponding single enantiomeric solution.

The natural auxin, indole-3-acetic acid (IAA) was also compared to IBA and always had substantially lower levels of activity than either IBA or ISA (Table 1). This data shows once again that the enantiomers of ISA have different activities and superior activities to either IBA or IAA.

This example was conducted in the same manner as in Example 2 above.

EXAMPLE 4

The example illustrates the effectivenss of various derivatives of indole-3-succinic acid.

The process recited in Example 1 was followed to make the derivatives and they were each tested in accordance with the procedure in Example 3 in a $10^{-7}$ M aqueous solution. The derivatives and their effectiveness compared to conventional auxins is reported below.

| Compound | Effectiveness |
|---|---|
| 4-chloroindole-3-succinic acid | 22× more effective than IAA and 3× more effective than indole-3-succinic acid |
| 5-chloroindole-3-succinic acid | 2× more effective than IAA |
| 5-bromoindole-3-succinic acid | same as IAA |
| 3'-indole-3-phenylpropanoic acid | 2× as effective as IAA |
| 3'-indole-3-methylpropanoic acid | same as IBA |

It will be understood that the claims are intended to cover all changes and modifications of the preferred embodiments of the invention herein chosen for the purpose of illustration which do not constitute a departure from the spirit and scope of the invention.

What is claimed is:

1. A method for promoting growth in plants comprising treating a plant with an effective amount of a compound of Formula 1 to promote growth in the plant, wherein Formula 1 is:

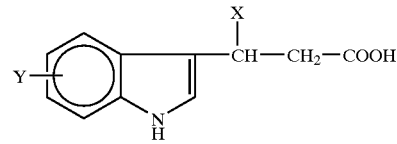

wherein:
Y is a hydrogen (H), a hydroxyl group (OH), a halogen, a nitro group ($NO_2$), a sulfinate group ($SO_3$), an alkyl group or an aryl group, and
X is a carboxylic acid group (COOH), a carboxylic acid ester group ($COOR_1$), an acetyl group ($CH_2COOH$) or an aryl group.

2. The method of claim 1 wherein the compound of Formula 1 is used as an enantiomer or a racemate.

3. The method of claim 1 wherein the compound of Formula 1 is in the form of a salt.

4. The method of claim 1 wherein the halogen group consists of fluorine (F), chlorine (Cl) and bromine (Br).

5. The method of claim 1 wherein the alkyl group is $C_1$ to $C_6$, and the aryl group is a phenyl or a naphthyl group.

6. The method of claim 1 wherein the treating comprises hydroponically growing the plant and the concentration of the compound of Formula 1 in aqueous solution is about $10^{-5}$ M to about $10^{-9}$ M.

7. The method of claim 1 wherein the treating comprises dipping the plant directly into an aqueous solution of the compound of Formula 1 at a concentration of 0.001 to 0.1% by weight.

8. The method of claim 1 wherein the treating comprises treating the soil in which the plant is grown with an aqueous solution having a concentration of the compound of Formula 1 at about one part per thousand to about one part per trillion.

9. A substantially pure enantiomer of indole-3-succinic acid or salt thereof.

* * * * *

UNITED STATES PATENT AND TRADEMARK OFFICE
CERTIFICATE OF CORRECTION

PATENT NO.   : 6,753,297 B2
DATED        : June 22, 2004
INVENTOR(S)  : Charles Hammer and Daniel Armstrong It is certified that error appears in the above-identified patent and that said Letters Patent is hereby corrected as shown below:

Title page,
Item [76], Inventors, change "Charloc" to -- Charles --

Signed and Sealed this

Twenty-first Day of December, 2004

JON W. DUDAS
*Director of the United States Patent and Trademark Office*